United States Patent [19]

Woodard et al.

[11] Patent Number: 5,620,869

[45] Date of Patent: Apr. 15, 1997

[54] METHODS FOR REDUCING INHIBITION OF NUCLEIC ACID AMPLIFICATION REACTIONS

[75] Inventors: Daniel L. Woodard, Raleigh, N.C.; Adriann H. Walters, Baltimore, Md.; Michael C. Little, Raleigh, N.C.

[73] Assignee: Becton, Dickinson and Company, Franklin Lakes, N.J.

[21] Appl. No.: 535,605

[22] Filed: Sep. 28, 1995

[51] Int. Cl.⁶ .............................. C12P 19/34; C12Q 1/68; C12Q 1/70; C07H 21/04
[52] U.S. Cl. .......................... 435/91.1; 435/91.2; 435/6; 435/5; 536/24.3; 536/24.32; 536/24.33
[58] Field of Search ................... 435/6, 91.2; 536/24.3, 536/24.33; 252/69

Primary Examiner—W. Gary Jones
Assistant Examiner—Dianne Rees
Attorney, Agent, or Firm—Donna R. Fugit

[57] ABSTRACT

It has been found that certain glycoproteins, particularly mucins, are inhibitors of nucleic acid amplification reactions and that inhibition of the amplification reaction is associated with partial degradation of the carbohydrate chain. Partial degradation of the carbohydrate of a non-inhibitory glycoprotein renders it inhibitory, and partial degradation of the carbohydrate of a slightly inhibitory glycoprotein makes it more inhibitory. Sample processing prior to amplification may contribute to partial degradation of the carbohydrate chains of the glycoproteins which are present and increase their inhhibitory effect. In contrast, complete removal of the carbohydrate significantly reduces or completely eliminates the inhibitory effect. Methods for reducing or eliminating glycoprotein-associated inhibition of nucleic acid amplification reactions are also disclosed.

8 Claims, No Drawings

METHODS FOR REDUCING INHIBITION OF NUCLEIC ACID AMPLIFICATION REACTIONS

FIELD OF THE INVENTION

The present invention relates to materials and methods for reducing or eliminating inhibition of nucleic acid amplification in biological samples.

BACKGROUND OF THE INVENTION

Nucleic acid amplification techniques have provided powerful tools for detection and analysis of small amounts of nucleic acids. The extreme sensitivity of such methods has lead to attempts to develop them for early diagnosis of infectious and genetic diseases, isolation of genes for analysis, and detection of specific nucleic acids in forensic medicine. Nucleic acid amplification techniques can be grouped according to the temperature requirements of the procedure. The polymerase chain reaction (PCR), ligase chain reaction (LCR) and transcription-based amplification require repeated cycling of the reaction between high (85° C.–100° C.) and low (30° C.–40° C.) temperatures to regenerate single stranded target molecules for amplification. In contrast, methods such as Strand Displacement Amplification (SDA), self-sustained sequence replication (3SR) and the Qβ replicase system are isothermal reactions which can be performed at a constant temperature. Conventional SDA (performed at lower temperatures, usually about 35°–45° C.) is described by G. T. Walker, et al. (1992a. *Proc. Natl. Acad. Sci. USA* 89, 392–396 and 1992b. *Nuc. Acids. Res.* 20, 1691–1696). A thermophilic version of the SDA reaction (tSDA, described below) has recently been developed, and is performed at a higher, but still constant, temperature using thermostable polymerases and restriction endonucleases. Thermophilic SDA is performed essentially as conventional SDA, with substitution of a thermostable polymerase and a thermostable restriction endonuclease. The temperature of the reaction is adjusted to a higher temperature suitable for the selected thermophilic enzymes and the conventional restriction endonuclease recognition/cleavage site is replaced by the appropriate restriction endonuclease recognition/cleavage site for the selected thermostable endonuclease.

Nucleic acid amplification reactions are very reproducible and highly efficient in "clean" systems where the target sequence to be amplified is in a compatible buffer and is essentially free of non-nucleic acid molecules. In a clinical setting, however, the target sequence is generally in a biological sample which also contains a wide variety of non-nucleic acid molecules (e.g., proteins, carbohydrates, lipids, etc.). Nucleic acid amplification in biological samples has often been inconsistent and variable, presumably because the other biological molecules which are present interfere partially or totally with the amplification reaction. This leads to false negative results and an inability to accurately quantify the amount of target sequence present. Further, a strongly positive sample may appear to be a weak positive in a sample where amplification is inhibited. These problems may make it difficult to accurately diagnose and effectively treat a patient based on the results of a test based on nucleic acid amplification.

Little is known about specific inhibitory molecules or the mechanisms of inhibition, however. For this reason prior art methods for reducing or eliminating inhibition of nucleic acid amplification in biological samples have been relatively non-specific and have been directed to the general removal or degradation of proteins in the sample. For example, phenol extraction of the biological sample has been used as a general method for removing hydrophobic proteins. Hydroxylated surfaces have been used to bind proteins for separation from the sample, and protease treatment has been used to non-specifically degrade proteins. In many cases, it is also possible to overcome the effect of inhibitors by diluting the sample prior to amplification. However, this approach also dilutes the target being amplified and thereby reduces the sensitivity of the assay. An alternative approach has been to isolate the nucleic acid from non-nucleic acid molecules, e.g., by binding to silica. While isolation of the nucleic acids may often successfully eliminate inhibitors of amplification, the process is time-consuming and recovery of the target is generally nonquantitative so the sensitivity of the assay is compromised. The success of such general methods has been variable, which may be at least partially attributable to varying amounts and types of inhibitory molecules in different biological samples.

It has been particularly difficult to obtain consistent nucleic acid amplification in sputum samples, as this type of biological sample is often especially inhibitory in the amplification reaction. Sputum is, however, a very important specimen for the diagnosis of pulmonary diseases such as tuberculosis. As they are generally very viscous (especially when pulmonary disease is present) sputum samples are typically liquified prior to analysis. A commonly used sample processing method for analysis of Mycobacteria in sputum is the N-acetyl-L-cysteine/sodium hydroxide method. This method uses NaOH, sodium citrate and N-acetyl L-cysteine (NALC) to liquify the sample, with recovery of the mycobacteria by centrifugation. The pellet is then resuspended in a small volume and used for culture or other diagnostic tests. Similar methods have been developed in which sodium hydroxide is used alone, with neutralization of the pellet prior to resuspension and analysis. NaOH has also been used with sodium lauryl sulfate (SLS) to process sputum samples, again with neutralization of the pellet by addition of acid prior to culture or other testing. In most cases, amplification inhibitors are found in the pellet after the centrifugation step, along with the Mycobacteria to be analyzed. The supernatant of a significant number of samples may also be inhibitory. These are the samples which present the greatest difficulty for nucleic acid amplification, as the results are inconsistent, variable and difficult to interpret.

It has now been discovered that certain glycoproteins, and mucins in particular, are significant inhibitors of nucleic acid amplification. Glycoproteins are proteins which contain covalently linked carbohydrate moieties. They are particularly prevalent in mammalian tissues. The carbohydrate chains of glycoproteins are mainly comprised of seven sugars: D-galactose, N-acetyl-D-galactosamine (GalNAc), D-glucose, N-acetyl-D-glucosamine, D-mannose, L-fucose, and sialic acid (N-acetylneuraminic acid, NGNA). The mucins are a type of glycoprotein with a complex carbohydrate structure containing disaccharide groups of N-acetylneuraminyl-(2→6)-N-acetylgalactosamine. Mucopolysaccharides (polysaccharides comprised of amino sugars or their derivatives) are also often found covalently bound to protein. Although the amino sugars of many mucopolysaccharides are the same as those found in glycoproteins, they are generally considered as a separate group of molecules because mucopolysaccharide-protein structures are much richer in carbohydrate than most glycoproteins. In the case of sputum samples, which often contain high concentrations of mucins, conventional sample processing methods such as liquification appear to increase the inhibitory effect of glycoproteins. The discovery of these mechanisms of amplification inhibition has led to the development of methods targeting glycoproteins to reduce their inhibitory effect.

SUMMARY OF THE INVENTION

It has been found that certain glycoproteins, particularly mucins, are inhibitors of nucleic acid amplification reactions. Certain mucopolysaccharides (glycosaminoglycans) which comprise the types of amino sugars found in inhibitory glycoproteins are also inhibitory. It has further been found that inhibition of the amplification reaction is associated with partial degradation of the carbohydrate chain. That is, partial degradation of the carbohydrate of a non-inhibitory glycoprotein renders it inhibitory, and partial degradation of the carbohydrate of a slightly inhibitory glycoprotein makes it more inhibitory. Sample processing prior to amplification may cause a non-inhibitory specimen to become inhibitory due to partial degradation of the carbohydrate chains of the glycoproteins which are present. In contrast, complete removal of the carbohydrate reduces or eliminates the inhibitory effect. Similarly, when the carbohydrate chains are intact as in the wild type glycoprotein structure, the molecules are generally not inhibitory. There exceptions among the wild type glycoproteins, however. Lectin, for example, is inhibitory to amplification even with the intact wild type carbohydrate structure. The inhibition of amplification associated with the partially degraded carbohydrate chains may be reduced or eliminated by 1) removal or dilution of the glycoprotein or mucopolysaccharide, 2) complete degradation of the carbohydrate chain (e.g., enzymatically), or 3) sample processing methods which maintain the wild type structure of the carbohydrate chain in samples which are not initially inhibitory.

DETAILED DESCRIPTION OF THE INVENTION

The effect of glycosaminoglycans and glycoproteins on the efficiency of nucleic acid amplification was studied in an attempt to determine the source of inhibition in unamplifiable sputum samples. A variety of glycosaminoglycans and glycoproteins (including mucins) were tested in conventional low temperature SDA model systems as described by Walker, et al., supra, for their effect on amplification. These compounds were tested at 5 µg/µL and 0.5 µg/µL in duplicate SDA reactions and detected in a chemiluminescent assay as described by C. A. Spargo, et al. (1993. Molec. Cell. Probes 7, 395–404). Bovine submaxillary mucin (BSM) Type I—S was the most inhibitory in conventional SDA, completely preventing amplification at 0.5 µg/µL. The second most inhibitory compound was bovine mucin Type II. Asialoglycophorin from human blood and bovine submaxillary mucin (BSM) Type I were moderately inhibitory, allowing amplification at low levels compared to positive controls. Asialomucins from bovine submaxillary gland and glycoprotein $\alpha_1$-acid from Cohn Fraction VI had little or no negative effect on amplification as evidenced by amplification at levels similar to positive controls. BSM Type II completely inhibited SDA at 5 µg/µL and reduced amplification about 75% at 0.5 µg/µL. Lectin (a plant glycoprotein) was also found to be inhibitory to conventional SDA at 5 µg/µL, 4 µg/µL, 3 µg/µL and 2 µg/µL. At 1 µg/µL amplification began to be detectable in the presence of lectin. Of the glycosaminoglycans, only heparin inhibited conventional SDA, and this inhibition was overcome by treatment with heparinase.

The other glycosaminoglycans tested (chitin, chondroitin sulfate B, keratin, hyaluronic acid, chondroitin sulfate A and chondroitin sulfate C) had no significant inhibitory effect. It appeared from this experiment that, in general, mucins are more inhibitory than human blood glycoproteins when spiked into conventional SDA reactions. A concentration effect was also demonstrated, as the inhibitory effect of some mucins and lectin was reduced upon dilution.

Thermophilic SDA was generally more sensitive to inhibition by the compounds tested than was conventional SDA, possibly due to increased inhibitory interactions or increased solubility of the inhibitory compounds at the higher temperature of thermophilic SDA. Wild type bovine submaxillary mucins completely prevented thermophilic SDA as they did conventional SDA, but asialo BSM which had little effect on conventional SDA reduced thermophilic SDA by about 76%. Similarly, the asialo and wild type human blood glycoproteins which had a minimal inhibitory effect on conventional SDA reduced thermophilic SDA by about 66%. Of the glycosaminoglycans, chitin, heparin and chondroitin sulfate B inhibited thermophilic SDA. As in conventional SDA, the other glycosaminoglycans tested (keratin, hyaluronic acid, chondroitin sulfate A and chondroitin sulfate C) were not inhibitory.

These results suggested that the sialic content of the glycoprotein might be related to the degree of amplification inhibition, as the more inhibitory glycoproteins (e.g., BSM Type I—S) in general have a higher sialic acid content than the less inhibitory glycoproteins (e.g., bovine submaxillary asialomucins) which have about 90% of the sialic acid removed. Porcine submaxillary mucin A⁻ (PSM A⁻, with sialic acid present) and asialo PSM (sialic acid enzymatically removed) were therefore tested at four different concentrations in conventional SDA to determine the effect of the sialic acid content of the glycoprotein. Aliquots of stock solutions (20 µL or 10 µL with 10 µL of water) of A⁻ PSM (4.1 µg/µL) and Asialo PSM (5.0 µg/µL) were added to 50 µL conventional SDA reactions. At the highest concentrations tested, asialo PSM reduced amplification by about 75%, whereas A⁻ PSM reduced amplification by about 50%, indicating that the content of sialic acid alone is unlikely to be a significant factor in the degree of amplification inhibition.

In a similar experiment we compared the inhibitory effect of six mucins which differed only in the composition and complexity of their carbohydrate structure. These molecules were prepared from PSM by selective enzymatic degradation of the associated carbohydrate chain using various glycosidases, as shown in the following table. The enzyme treatment used to produce Apo PSM was effective to completely remove all carbohydrate from 99% of the glycoprotein molecules. About 1% had a residual GalNAc residue linked to the protein.

| MUCIN | CHO STRUCTURE |
| --- | --- |
| A⁺ PSM (4.1 µg/µL) | intact CHO, most complex |
| A⁻ PSM (4.1 µg/µL) | terminal GalNAc removed with hexosaminidase |
| Asialo PSM (5.0 µg/µL) | sialic acid (NGNA) removed with neuraminidase |
| Afuco PSM (1.0 µg/µL) | fucose removed with 1,2 α-fucosidase |
| Apo PSM (2.08 µg/µL) | all CHO removed with o-glycanase, neuraminidase, hexosaminidase and 1,2 α-fucosidase |
| BSM (5.0 µg/µL) | intact CHO, most complex |

Aliquots of 20 µL, 10 µL or 1 µL were spiked into 50 µL SDA reactions as before and detected in a chemiluminescent assay. The SDA positive control sample gave a result of 26,481 RLU (relative light units). A⁺ PSM and BSM (wild type mucins) were not inhibitory in this experiment, although BSM had appeared to be inhibitory previously. The BSM in this experiment was purchased from a commercial source (Sigma Chemical Company, St. Louis, Mo.), whereas the inhibitory BSM tested previously was produced in the laboratory. It is possible that differences in methods of preparation result in BSM's with different carbohydrate structures and thereby influence the inhibitory properties of this glycoprotein. Apo PSM was also not inhibitory to amplification. A⁻ PSM, Afuco PSM and Asialo PSM were all inhibitory, with A⁻ PSM having the greatest effect. Afuco PSM showed some inhibitory effect at both concentrations, and Asialo PSM was the least inhibitory. The results are shown below:

| MUCIN | RLU (20 µL) | RLU (10 µL) |
|---|---|---|
| A⁻ PSM | 182.4 | 10,509.0 |
| Afuco PSM | 2,119.0 | 4,257.0 |
| Asialo PSM | 2,728.0 | 6,109 |

These results indicated that the level of amplification inhibition associated with mucins was related to the structure of the carbohydrate chain, with partially degraded carbohydrate chains being associated with the inhibitory effect. Either intact (wild type) carbohydrate structure or a complete absence of carbohydrate appeared to overcome the inhibitory effect in the conventional SDA reaction. Elimination of the inhibitory effect by removal of essentially all carbohydrate from the glycoprotein is not believed to be related to the particular enzymatic treatment used in this experiment. Other glycosidases or other carbohydrate-cleaving enzymes which would render the glycoprotein essentially carbohydrate-free would also be expected to overcome the inhibitory effect.

These results also suggested that methods used for processing a biological sample prior to amplification may affect the degree of amplification inhibition which is observed. It was hypothesized that sputum, where high concentrations of mucins are often found, may be particularly sensitive to the effects of sample processing. As sputum is typically treated with NALC and proteinase K prior to most diagnostic testing, we evaluated the effect of these treatments on the inhibitory properties of mucins. BSM Type I—S and BSM Type II in varying amounts were incubated with an equal volume of NALC, neutralized, and centrifuged. The supernatants were removed and discarded. The pellet was then reneutralized, centrifuged and treated with proteinase K in KPDG buffer at 55° C. for 30 min. After inactivating the proteinase K at 100° C. for 5 min., the sample was used in the SDA reaction. This treatment duplicated typical sputum sample processing. Treated samples exhibited significantly increased levels of amplification inhibition as compared to untreated samples, as shown below. The positive control was 10,724 RLU and background chemiluminescence was about 10–14 RLU.

| | AMOUNT OF MUCIN ADDED | | |
|---|---|---|---|
| | 25 µL | 15 µL | 5 µL |
| BSM Type I-S | 10.7 | 5.8 | 9.0 |
| BSM Type II | 18.8 | 19.1 | 261.2 |

This experiment confirmed that sample processing methods may increase inhibition of amplification in a biological sample. The inhibitory glycoproteins survive the NALC treatment in a form which is more inhibitory than without such treatment. NALC and/or protease K treatment may therefore contribute to partial degradation of the carbohydrates of the glycoproteins during sample processing, thus increasing their inhibitory effect.

Additional experiments were conducted to evaluate the mechanism by which glycoproteins inhibit nucleic acid amplification reactions. A filter binding assay was used to study the binding of target DNA to mucins with different carbohydrate structures. Briefly, kinased DNA in buffer containing various levels of mucins was filtered through nitrocellulose. If the mucin did not bind to the DNA, the DNA was not retained on the filter. Binding of the mucin to the DNA caused it to be retained on the filter in an amount which was indicative of the affinity of the mucin for the DNA. Quantitative results were obtained by detecting the amount of radioactivity retained on the filter. To perform the experiments, target DNA was kinased and mixed in solution with one of the following glycoproteins: human blood glycoproteins (noninhibitory), A⁻ PSM (inhibitory only at high concentrations), BSM Type I—S (highly inhibitory), A⁺ PSM (noninhibitory) and BSM (noninhibitory). A clinical sputum sample which significantly inhibited amplification was also tested. BSM Type I—S bound about 37.45% of the DNA, whereas the human blood glycoproteins did not detectably bind to the target. A⁻ PSM (a weak inhibitor of amplification), A⁺ PSM and BSM bound DNA at low levels. The inhibitory sputum sample bound about 12% of the DNA target. These experiments suggested that degradation of the carbohydrate may increase the affinity of the glycoprotein for nucleic acids and that binding to the target may interfere with the enzymatic processes of amplification.

Polymerase activity in the presence of glycoproteins was also evaluated by determining the efficiency of incorporation of deoxynucleoside triphosphates. One unit of polymerase is defined as the amount which will incorporate 10 nmoles of deoxynucleoside triphosphate (dNTP) in 30 min. The activity of exo⁻ Klenow polymerase was tested in a polymerase extension assay using a sputum sample which was completely inhibitory to amplification (Sample 7688) and two sputum samples which were not inhibitory to amplification (Samples 7689 and 12122). Radioactively labeled dNTPs ($4 \times 10^{-6}$ nmoles/cpm) were added to the sample with activated calf thymus DNA (i.e., treated with DNase) to serve as a template for the polymerase. A predetermined number of units of polymerase was added to the amplification reaction for each sputum sample and an uninhibited positive control reaction (isolated DNA amplified in buffer). The apparent activity of the polymerase activity during amplification in each sample and the positive control was determined based on the amount of radioactivity incorporated as a function of time. The experimental value in cpm of the positive control was compared to the experimental value in cpm of the clinical samples to determine if exo⁻ Klenow activity was effected by the sputum samples. The results are shown below:

| SAMPLE | CPM | % OF CONTROL ACTIVITY |
|---|---|---|
| 10 µL Sample 7688 | 1,654 | 49.3% |
| 50 µL Sample 7688 | 469 | 85.6% |
| 10 µL Sample 7689 | 3,619 | uninhibited |
| 50 µL Sample 7689 | 4,207 | uninhibited |
| 10 µL Sample 12122 | 4,372 | uninhibited |

| SAMPLE | CPM | % OF CONTROL ACTIVITY |
|---|---|---|
| 50 µL Sample 12122 | 4,210 | uninhibited |
| Positive Control | 3,267 | |

The inhibitory clinical sample significantly reduced the activity of the polymerase in a concentration dependent manner. Dilution of the inhibitory sample resulted in increased polymerase activity, indicating that a reduction in the concentration of the inhibitor was associated with an increase in polymerase activity. Polymerase activity was normal (i.e., equivalent to the uninhibited positive control ) in noninhibitory sputum samples. The results of these experiments suggested that the mechanism of inhibition is related to interference with the DNA synthesizing activity of the polymerase during amplification. This may not be the only effect of partially degraded glycoproteins, however, as additional inhibitory mechanisms have not been ruled out.

Before the source of amplification inhibition in clinical samples was determined, several conventional methods for removing amplification inhibitors were applied to Sample 7688. These included protease K treatment, treatment with lipase #7 and protease K, treatment with lipase #6 and protease K, washing the NALC pellet with ethanol, protease K treatment and washing the NALC pellet with ethanol, washing the NALC pellet with EGTA and EDTA, and EGTA/EDTA washing after protease K treatment. It is now known that these sample treatments (e.g., protease K), which are conventional for reducing or eliminating amplification inhibition in clinical samples, may increase amplification inhibition if glycoproteins are present in the sample. However, new methods have now been discovered which reduce or eliminate the inhibitory effect of glycoproteins in general, and mucins in particular.

First, it was discovered that amplification inhibition could be reduced or eliminated by treating a glycoprotein-containing sample with an anionic solid phase, often restoring normal levels of amplification. The inhibitory glycoproteins apparently bind to anionic surfaces, allowing their physical separation from the sample prior to nucleic acid amplification. Cation exchange resins (e.g., carboxymethyl, phospho or sulphopropyl derivatized ion exchange matrices) or any other negatively charged surfaces are useful for this purpose. Methods for binding cationic molecules to cation exchange resins and other negatively charged surfaces, and methods for separating them from the remainder of the sample are known in the art. These include column chromatography and batch processes (e.g., mixing the sample with the solid phase and sedimenting the solid phase with the bound inhibitors by centrifugation, settling, magnetic separation or similar means). These methods are generally applicable to separation of the inhibitory glycoproteins from samples prior to amplification, allowing the flow-through from the cation exchange column or the supernatant of the batch process to be used in the nucleic acid amplification reaction.

Negatively charged silicaceous materials may also be used to bind the inhibitory glycoproteins for physical separation from the sample. In one embodiment, useful anionic silicaceous materials may be prepared as described in U.S. Pat. No. 5,342,931. These anionic silicas are prepared by adding an alkaline solution to a silicaceous material (e.g., $SiO_2$ or an $SiO_2$ derivative in the form of diatoms, glass beads or glass fiber membranes) and heating. The method is not limited to any particular form of silica or to any particular alkaline solution. The alkaline solution may comprise NaOH, KOH, sodium hydride or any similar reagent which produces hydroxide ions in aqueous solution. The molar ratio of alkali to silicaceous material is about 0.1:1 to 10:1, preferably 2:1 to 10:1. Dissolution of the silicaceous materials increases as the proportion of alkali increases, however. Ratios of alkali:$SiO_2$ above 10:1 may result in complete dissolution of the particles or production of silicaceous particles which are too small for efficient binding and separation of the inhibitory glycoproteins depending on the initial size of the silica particles, the concentration of alkali, the reaction temperature and the length of time of the reaction. These reaction parameters may be routinely adjusted to obtain anionic silicaceous materials with the particle size desired.

The silicaceous material is heated in the alkaline solution, preferably by refluxing, for a period of time sufficient to add hydroxide ions to the $SiO_2$ lattice. The time required for the reaction will vary depending on the concentration of hydroxide ion in the alkaline solution and the temperature of the reaction. Lower concentrations of hydroxide ion and/or lower temperatures require longer reaction times, whereas higher concentrations of hydroxide ion and/or higher temperatures reduce the reaction time. In general, refluxing the alkaline suspension for 48 hours is sufficient over a wide range of hydroxide ion concentrations. The final product is recovered by filtering, washing and drying. Water, acetone, nucleic acid reaction buffers and the like are suitable washing reagents. The anionic silicaceous material may then be used for binding and separation of inhibitory glycoproteins. Preferably, binding of the inhibitors is conducted at approximately neutral or alkaline pH to avoid protonation of the anionic surface which would favor binding of DNA. As NALC processing of sputum samples results in a highly alkaline environment (about pH 14) it may be possible to add the silicaceous starting material to the sputum sample such that the silicaceous material reacts with the alkali present in the sputum sample and the desired anionic silicaceous material is produced, binding glycoprotein inhibitors of nucleic acid amplification. Most preferably, for biological samples, binding is conducted at about pH 6.5–8.5. The chemical structures of the starting material and final product are illustrated below for a representative silicaceous material:

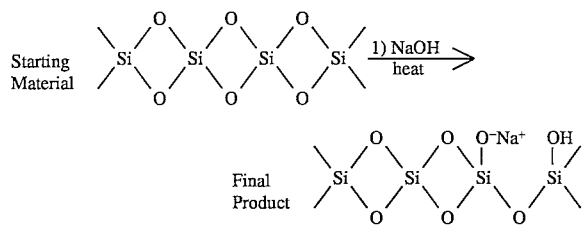

Anionic diatoms prepared as described above were mixed with the NALC/proteinase K treated solutions of BSM Type I—S and BSM Type II previously prepared and with a clinical sputum sample which was completely inhibitory to amplification (Sample 3699) in a pH 7.6 buffer. After incubation with the anionic diatoms, the samples were centrifuged and the supernatants were added to amplification reactions reactions as before. The treated BSM Type I—S and BSM Type II supernatants were amplified by SDA as described above. The inhibitory clinical sample supernatant was amplified by PCR using conventional methods. Amplification was detected in the chemiluminescent assay with the following results:

|  | RLU | | |
| --- | --- | --- | --- |
|  | 20 µl super | 10 µl super | 5 µl super |
| Sample 3699 (PCR) | | | |
| w/o anionic diatoms | 172 | 31,981 | — |
| w/anionic diatoms | 10,205 | 67,160 | — |
| BSM Type I-S (SDA) | | | |
| w/o anionic diatoms | 6.5 | NA | 11.2 |
| w/anionic diatoms | 1,099 | 9,589 | 8,254 |
| BSM Type II (SDA) | | | |
| w/o anionic diatoms | 32.4 | NA | 2,277 |
| w/anionic diatoms | 15.2 | 655 | 3,228 |

The positive control (a clean buffer system without added inhibitors) gave an RLU of 9,663. The treatment with anionic diatoms therefore successfully removed inhibitors, allowing significant increases in the level of amplification. Amplification inhibition was completely eliminated in the clinical sample after treatment with anionic diatoms and post-treatment amplification exceeded the positive control. In the BSM Type I—S sample amplification was restored to the level of the positive control at the two lowest concentrations of inhibitor. At the highest concentration (20 µL) amplification was significantly improved by treatment with anionic diatoms (about 170 fold), but was still less than the positive control. For BSM Type II (previously identified as the most inhibitory mucin tested), amplification was not restored by anionic diatom treatment at any of the concentrations tested. These results indicate that the binding capacity of the anionic diatoms may have been exceeded in the high concentration BSM Type I—S sample and in all of the BSM Type II samples.

Anionic siliceous materials may also be in the form of filters. In this embodiment, the inhibitory clinical sample may be filtered through the anionic filter prior to amplification such that inhibitors are bound to the filter and thereby removed from the filtrate. Alternatively, a particulate anionic siliceous material may be supported on a conventional filter and the sample passed through (e.g., by centrifugation) such that inhibitors are bound to the anionic siliceous material.

Anionic siliceous materials in the form of beads such as those used to disrupt bacterial cells may serve two functions when processing samples for nucleic acid amplification. Siliceous beads suitable for disruption of cells (e.g., glass or zirconium silicate) may be treated as described above to produce anionic materials, using reaction conditions which avoid dissolution of the beads to an extent which would preclude their use for cell disruption. The anionic siliceous beads may then be added to a clinical sample suspected of containing the cells of interest and used to disrupt the cells while at the same time binding inhibitors of amplification which may be present. Cells are typically disrupted by sonicating or vortexing the sample containing the beads, but other suitable methods are known in the art. Following disruption of the cells, the anionic beads with bound inhibitors are separated from the sample, typically by filtration or sedimentation. Nucleic acids, which are also negatively charged, do not bind to the anionic surfaces of the beads and remain in the liquid phase for amplification.

Alternatively, glycoprotein inhibitors may be removed or eliminated from the sample by treating with glycosidases to completely remove carbohydrate from the inhibitory glycoproteins. To ensure removal of all glycosidic residues when the exact carbohydrate structure is not known, a mixture of glycosidases is preferred (e.g., n-glycosidase, o-glycosidase and neuraminidase). Carbohydrate may be essentially completely removed from mucins by either sequential or simultaneous treatment of the glycoprotein with o-glycanase, 1,2 α-fucosidase, hexosaminidase and neuraminidase. This treatment removes all carbohydrate from the mucin except for a single GalNAc residue linked to the protein in about 1 of 100 glycoprotein molecules. Typically, the enzymes are mixed with the sample containing glycoprotein and incubated for a period of time sufficient for degradation of the glycosidic bonds (e.g., about 1 hour at pH 7.6).

Chemical methods for removing carbohydrate from glycoproteins are known and may also be useful in the invention. For example, the sample may be treated with trifluoromethane sulfonic acid at 4° C. under anhydrous conditions or it may be subjected to Smith degradation (sodium periodate treatment followed by hydrolysis with a weak acid). These methods may be employed during NALC treatment of a sputum sample. As Mycobacteria remain intact during NALC processing, their nucleic acids should be protected from deleterious effects of the chemical treatment. Residual chemicals, which may also inhibit amplification, may then be washed out of the NALC pellet prior to lysing the Mycobacteria and amplifying the target nucleic acid.

What is claimed is:

1. A method for amplifying nucleic acids in a sample containing nucleic acid amplification inhibitors comprising:
   a) contacting the sample with an anionic silicaceous material such that the nucleic acid amplification inhibitors are bound to the anionic silicaceous material;
   b) separating the anionic silicaceous material and the nucleic acid amplification inhibitors bound thereto from the sample, and;
   c) amplifying the nucleic acids contained in the sample.

2. The method of claim 1 wherein the anionic silicaceous material is selected from the group consisting of anionic glass beads, anionic glass filters anionic zirconium silicate beads and anionic diatoms.

3. The method of claim 1 wherein the anionic silicaceous material is separated from the sample by filtration or sedimentation.

4. The method of claim 1 wherein the anionic silicaceous material is a filter.

5. The method of claim 1 wherein the nucleic acids are contained in cells in the sample and the cells are disrupted using the anionic silicaceous material.

6. The method of claim 5 wherein the anionic silicaceous material is selected from the group consisting of anionic glass beads and anionic zirconium silicate beads.

7. A method for amplifying nucleic acids in a sample containing glycoprotein inhibitors of nucleic acid amplification comprising:
   a) treating the sample with one or more glycosidases such that carbohydrate is substantially completely removed from the glycoprotein, and;
   b) amplifying the nucleic acids in the treated sample.

8. The method of claim 7 wherein the one or more glycosidases are selected from the group consisting of o-glycanase, hexosaminidase, 1,2 α-fucosidase and neuraminidase.

* * * * *